United States Patent [19]

Ludlow et al.

[11] Patent Number: 5,089,714
[45] Date of Patent: Feb. 18, 1992

[54] PARTICLE ASYMMETRY ANALYSER HAVING SPHERICITY DETECTORS

[75] Inventors: Ian K. Ludlow, Welwyn Garden City; Paul H. Kaye, Kimpton, both of England

[73] Assignee: The Secretary of State for Defence in Her Britannic Majesty's Government of the United Kingdom of Great Britain and Northern Ireland, London, England

[21] Appl. No.: 476,396

[22] PCT Filed: Nov. 10, 1988

[86] PCT No.: PCT/GB88/00975
§ 371 Date: Jun. 4, 1990
§ 102(e) Date: Jun. 4, 1990

[87] PCT Pub. No.: WO89/04471
PCT Pub. Date: May 18, 1989

[30] Foreign Application Priority Data

Nov. 10, 1987 [GB] United Kingdom ............... 8726304

[51] Int. Cl.⁵ ................................. G01N 15/06
[52] U.S. Cl. ................... 250/574; 250/575; 356/343
[58] Field of Search ........... 250/574, 575; 356/338, 356/336, 341, 342, 343

[56] References Cited

U.S. PATENT DOCUMENTS

| | | | |
|---|---|---|---|
| 3,431,423 | 3/1969 | Keller | 356/338 |
| 3,457,407 | 7/1969 | Goldberg | 250/575 |
| 3,781,552 | 12/1973 | Kadrmas | 356/338 |
| 4,251,733 | 2/1981 | Hirleman, Jr. | 250/575 |
| 4,273,443 | 6/1981 | Hogg | 250/574 |
| 4,422,761 | 12/1983 | Frommer | 356/338 |
| 4,523,841 | 6/1985 | Brunsting et al. | 356/343 |
| 4,606,636 | 8/1986 | Monin et al. | 356/338 |
| 4,850,707 | 7/1989 | Bowen et al. | 356/338 |
| 4,890,920 | 1/1990 | Niziolek et al. | 356/336 |

FOREIGN PATENT DOCUMENTS 2535051A 4/1984 France.
2041516A 9/1980 United Kingdom.

OTHER PUBLICATIONS

International Search Report (PCT/GB88/00975-Feb. 8, 1989).

Primary Examiner—David C. Nelms
Assistant Examiner—Que T. Le
Attorney, Agent, or Firm—Nixon & Vanderhye

[57] ABSTRACT

An apparatus and method which provides a measure of the asymmetry as well as the size of individual fluid borne particles. Laser-light scattering techniques are employed to obtain data on the particles, which is then compared to data on known particle shapes to ascribe an asymmetry factor to the particles.

15 Claims, 2 Drawing Sheets

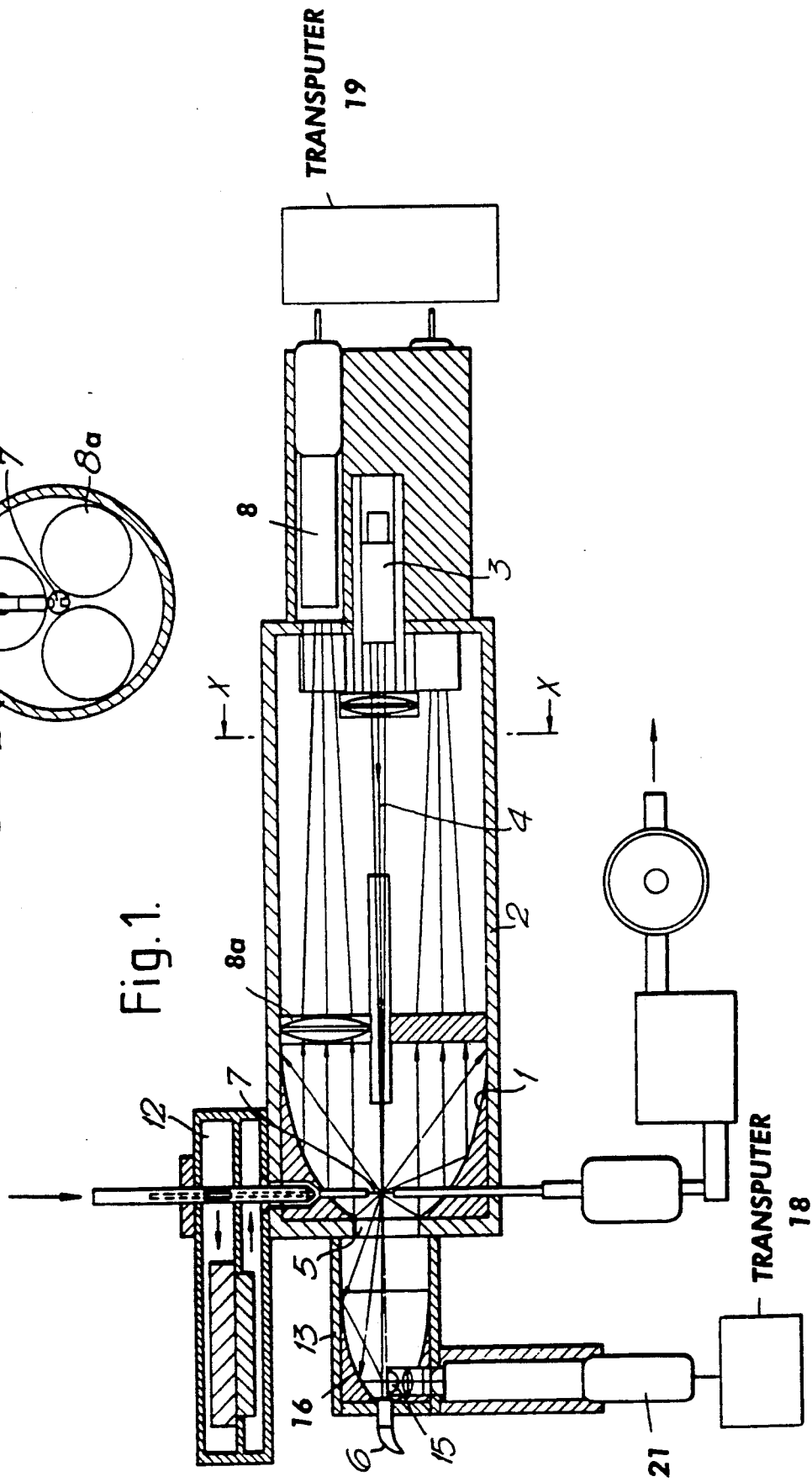

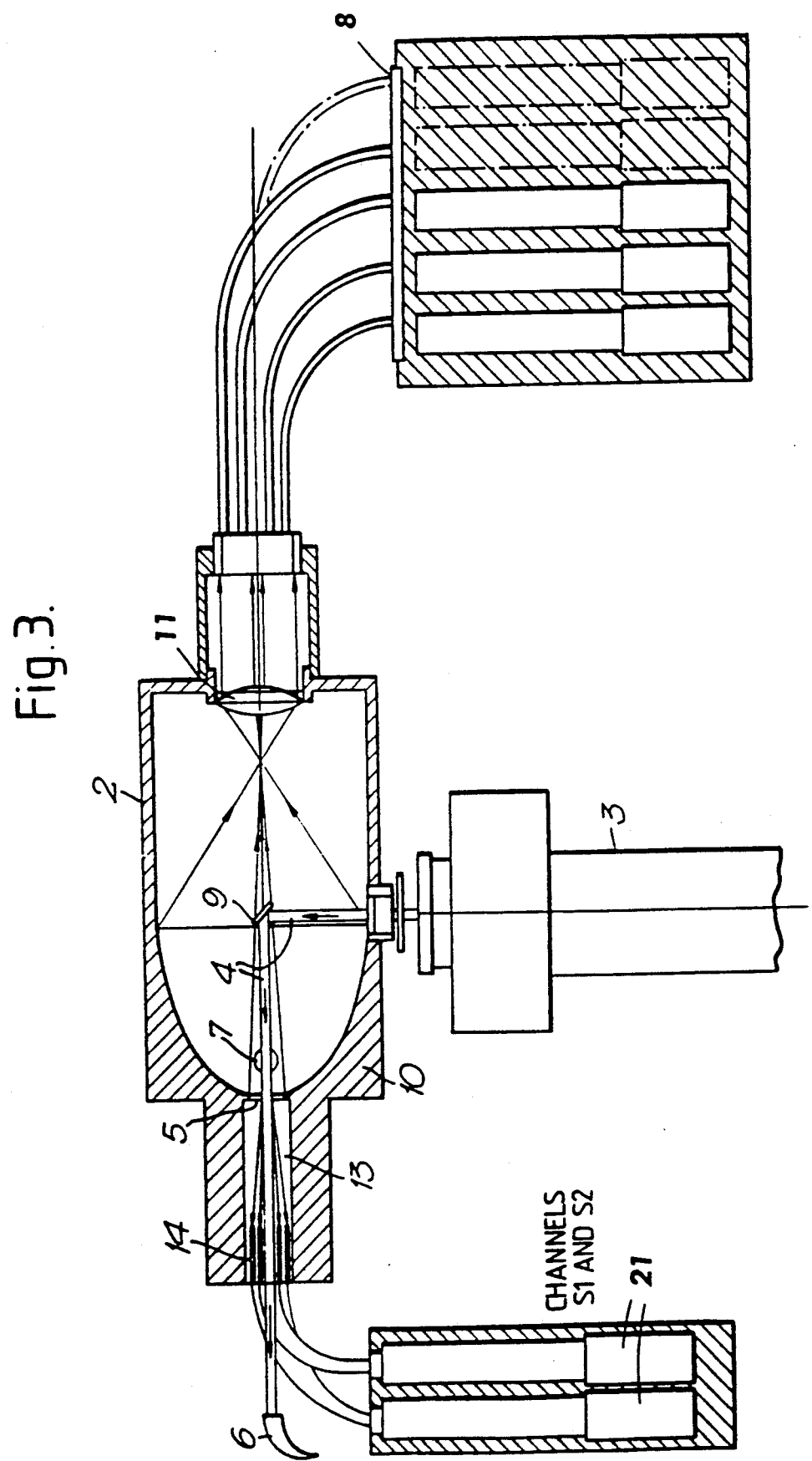

PARTICLE ASYMMETRY ANALYSER HAVING SPHERICITY DETECTORS

BACKGROUND OF THE INVENTION

1. Field of the Invention

This invention relates to the techniques for the analysis of fluid-borne particles and particularly for looking at the asymmetry of such particles. For example, in the study of aerosols, aerosol dispersions and airborne particulate pollution control, there is a requirement for the rapid determination of particle size distribution especially in the diameter range 1 to 10 microns, together with some knowledge of the geometry and symmetry of individual particles. The latter information could, for example, enable particles with spherical symmetry to be identified and thus allow the counting/monitoring of liquid droplets in an environment including other solid, non-spherical particles. In the context of the present specification, the term particles is intended to apply both to solid bodies and to drops of liquid.

It is desirable for such techniques to be able to count individual particles in a sample at rates of, typically, 20,000 particles per second, to be able to distinguish between spherical and non-spherical particles in the sample and to count each type. Another desirable feature is to categorise spherical particles having diameters of 0.5-15 microns into a number of size bands and also in this connection to classify particle coincidences as 'non-spherical' and hence to ignore them in the compilation of size spectra.

2. Discussion of Prior Art

The normal techniques for the examination of particles, as used in several instruments available commercially, employ the detection and analysis of electromagnetic radiation scattered by the particles. All such instruments use a mechanical mechanism to drive the sample air through a "sensing volume" where the carried particles are illuminated by the incident electromagnetic radiation. The radiation scattered by the particles is received by one or more detectors which convert the engergy to electrical signals from which information may be extracted by appropriate electrical circuits.

One class of instrument available commercially permits the collection of scattered radiation from large numbers of particles simultaneously, and uses this information to determine a mean figure for particulate mass per unit volume of gas or air, or the statistically averaged size distribution of particulate matter. These instruments are not capable of examining individual particles, and therefore cannot yield accurate particle counts or information relating to particle morphology.

A second class of instrument uses the properties of laminar flow in gases to restrict the particles to a smaller sensing volume and then, by focusing the incident electro-magnetic radiation in some way, is capable of the examination of individual particles, yielding a particle count and possibly approximate size distribution.

The prior art instruments, therefore, will give, to a certain extent, information on particle size and particle count. However, there is no instrument available that is capable of giving information on the asymmetry of individual fluid-borne particles.

There is therefore a need for a particle analyser which can analyse individual fluid-borne particles and give information as to the assymmetry of the particles by, for example, ascribing an asymmetry factor to the individual particles.

SUMMARY OF THE INVENTION

According to one aspect of the present invention there is provided a particle analyser for use in determining the asymmetry of particles characterised in that it includes means for delivering a sample of airborne particulates in the form of a laminar flow fluid, means for illuminating the sample with a randomly or circulary polarised laser beam, means for reflecting and directing scattered radiation on to at least one forward scattering detector and at least three sphericity detectors placed symmetrically about a central axis; means for deriving data from the detectors to describe the particle and comparing the data with data on known shapes to determine the degree of particle asymmetry.

The scattered radiation is reflected by a concave reflector, preferably an ellipsoid mirror which directs the radiation towards radiation collectors. Radiation scattered at low angles is detected in a second chamber, which leads from an aperture in the ellipsoid mirror, by radiation collectors, preferably optical fibres arranged concentrically around the unscattered beam. The radiation collected is then converted into electrical signals, processed and analysed and by comparing with data on known particle shapes the particles are ascribed an asymmetry factor.

Furthermore, in addition to the asmmetry factor the size of the particle may also be determined. A large number of particles may be ascribed an asymmetry factor, and the cumulative results of this operation coupled with the associated size spectra, could be used to generate a topographical 'thumb print' of the particles in an environment which may be of more value than the data of single particles taken alone.

In looking for sphericity, the criterion for classification for spherical particles can be defined readily as symmetrical scattering about the axis of the illuminating beam of randomly polarised or circularly polarised radiation. Therefore a number of radiation collectors are placed radially symmetrically about the reflection axis of the concave reflector.

In looking for the degree of asymmetry, the arrangement of the collectors could not be assumed to be the optimum for particle asymmetry analysis. The design of the scatter chamber must allow for the flexibility collector configurations specifically required, and the positions of which to be varied at will.

The advantage of this technique is that, by using optical fibre collection optics, one can readily simulate the effect of placing almost any number of collectors at any position around most of the scattering sphere, a task which would otherwise be mechanically extremely difficult. Thus with a high degree of flexibility, various detection geometries may be tested without the need for mechanical changes to the chamber itself.

According to a second aspect of the present invention a method of determining the asymmetry of particles characterised in that it includes the steps of:

providing a sample of airborne particulates in the form of a laminar flow; illuminating the sample with a randomly or circularly polarised laser beam; reflecting the radiation scattered by individual particles to at least one forward scattering detector and at least three sphericity detectors placed radially symmetrically about a central axis; deriving data from the detectors describing the particle; and comparing the data with data on known shapes to determine the degree of particle asymmetry.

The sample may be an aerosol.

BRIEF DESCRIPTION OF THE DRAWINGS

Two embodiments of the invention will now be described by way of example only and with reference to the accompany drawings of which:

FIG. 1 is a schematic side view in section of a particle analyser for analysing spherical particles.

FIG. 2 is a sectional view of the analyser in FIG. 1 along the line x—x.

FIG. 3 is a schematic side view in section of an asymmetry analysis system.

DETAILED DISCUSSION AND PREFERRED EMBODIMENTS

FIG. 1 illustrates a basic form of the invention where only spherical particles are analysed in which a parabolic concave reflector (1) is located at one end of a scatter chamber (2). Mounted at the other end of the scatter chamber (2) and aligned with the principal axis of the reflector (1) is a laser (3), which directs a beam of radiation (4) towards a hole (5) in the reflector (1) and chamber (2) at the principal axis of the reflector. After passing through the hole (5) the beam (4) enters a beam dump (6), typically a Rayleigh horn.

A sample (7) of laminar flow air is directed into the chamber (2) to intercept at right angles the laser beam (4) at the focal point of the parabolic reflector (1).

A particle in the sample (7) will deflect the radiation out of the beam (4) onto the reflector (1) which reflects it parallel to the principal axis to radiation collectors (8) adjacent the laser (3). The radiation collectors (8) may be photo multiplier units, optical fibres leading to such units, or lenses (8a) for directing the light onto fibres or units.

As shown in FIG. 2 three radiation collector lenses 8a are arranged radially around the beam 4. In such an arrangement symmetrical scattering can be directed which will identify spherical particles. Indeed, any number of lenses 8a and corresponding radiation collectors 8 may be arranged radially about the beam of radiation 4.

FIG. 3 shows a preferred embodiment of a particle analyser according to the present invention which is able to analyse individual particles and ascribe to them an asymmetry factor. In this embodiment, the laser (3) is mounted beneath the chamber (2) and at 90° to principal axis of the reflector (1). The beam (4) being reflected onto the principal axis of the reflector by a prism or mirror (9) suitably positioned on the axis. Indeed, the laser (3) may be mounted just about anywhere about the scatter chamber (2) with a appropriately angled mirror (9) on the axis.

FIG. 3 also illustrates the scatter chamber (2) having an ellipsoid reflector (10) being one focal point of the ellipse and a collector lens (11) mounted near the second focal point to render parallel the reflected radiation to radiation collectors (8) at the end of the chamber (2). At this point the intensity distribution represents a spatially modified replica of that scattered into approximately 0.84 of a sphere by the particle. Figure one illustrates the sample (7) of fluid being delivered in laminar flow, by means of a sheath air intake (12) supplying a layer of air at a constant velocity.

A certain amount of difficulty is experienced in capturing and analysing the radiation scattered at low angles to the beam (4) direction. At very low angles (1° to 3°) they are swamped by light scattering from laster focussing optics. To overcome this a second scattering chamber (13) is introduced coaxial to the principle axis of the concave reflector (1) on the main scatter chamber (2). Radiation detector 21 are suitably placed in this chamber to collect the low angle deflections.

FIG. 3 therefore illustrates a second chamber (13) in which optical fibres (14) are arranged around the beam (4). The optical fibres (14) may be arranged in concentric rings around the beam (4). The fibres (14) act radiation to collect radiation and direct it to detectors 21 for converting the radiation collected into electrical signals for processing and analysis.

As illustrated in FIG. 1, the second chamber (13) may alternatively have a second concave reflector (16), which would normally be ellipsoided, having the point & intersection of the beam (4) and the sample (7) as its second or distal focal point and having a radiation collector (15) at its first or proximal focal point. Thus radiation deflected at low angles will strike the ellipsoidal reflector and be directed onto the radiation collector (15) and focussed onto detector 21.

The radiation collector (15) may be positioned at 90° to this direction as shown in FIG. 1. The latter arrangement would collect relatively more radiation of low angle of deflection, but less overall since only deflections in the direction of the face of the collector will be recorded.

FIG. 1 illustrates how in use the sample (7) is supplied in laminar flow by means of a sheath of constant velocity filtered air being supplied around the sample. Thus the outer parts of the sample flow at the same velocity as the inner parts. The outer parts of the sample would otherwise flow more slowly due to friction with the stationary air next to the sample flow. Additionally, and more importantly the coaxial tube supplying the sheath of air is designed to dynamically focus the particles in the sample to provide a laminarflow of particles. Thus making it easier to line up the particle flow on the focal point of the reflector.

The asymmetry particle analyser operates as follows. The laser beam, produced by a gas laser, enters the chamber at right angles to the reflector axis and is reflected through 90° along the principal axis of the reflector. The radiation scattered by individual particles from approximately 19° to 145° relative to the beam axis is thus reflected onto the aspheric collection lens at the rear of the chamber. This lens renders the emerging light parallel, and the intensity distribution across this output window represents a spatially modified replica of that scattered into approximately 0.84 of a sphere by the particle.

With the collected light in the form described above, the positions of the optical fiber detectors to measure the light distribution may be varied at will.

To determine particle sphericity the detectors would be placed symmetrically about the axis of the output window.

In this way, with the use of optical fibre optics, one can readily simulate the effect of placing almost any number of detectors at any position around most of the whole scattering sphere.

Based upon the results of theoretical models and experimental results of scattering patterns of known shapes, algorithms are used to ascribe to particles an asymmetry factor.

The processing of data from particles to determine their asymmetry could be handled by a transputer 18, 19 as produced for example by the British Inmos chip manufacturers.

One transputer is used for each detection channel. In this way, tasks hitherto performed serially on incoming data from channels could be performed on all channels simultaneously giving a substantial increase in data throughput.

Although this invention has been described by way of example and with reference to possible embodiments thereof, it is to be understood that modifications or improvements may be made without departing from the scope of the invention as defined in the appended claims.

We claim:

1. A particle analyser for use in determining the asymmetry of particles, said analyser includes:
   means for providing a sample of airborne particulates in the form of a laminar flow;
   means for illuminating the sample with a polarised laser beam;
   at least one forward scattering detector and at least three sphericity detectors placed radially symmetrically about a central axis;
   means for directing the radiation scattered by individual particles towards said scattering and sphericity detectors; and
   means for deriving data from the detectors to describe the particle.

2. A particle analyser as claimed in claim 1 wherein the means for directing the radiation is a concave reflector.

3. A particle analyzer as claimed in claim 2 wherein the concave reflector is an ellipsoid reflector.

4. A particle analyser as claimed in claim 2, wherein the central axis is the reflection axis of the reflector.

5. A particle analyser as claimed in claim 1 wherein the detectors are photmultipliers.

6. A particle analyser as claimed in claim 1 wherein the detectors are optical fibres leading to photomultiplers.

7. A particle analyser as claimed in claim 1 wherein the radiation collectors may take any configuration and their positions may be varied at will.

8. A method of determining the asymmetry of particles wherein said method includes the steps of:
   providing a sample of airborne particulates in the form of a laminar flow;
   illuminating the sample with a polarised beam;
   reflecting the radiation scattered by individual particles to at least one forward scattering detector and at least three sphericity detectors placed radially symmetrically about a central axis; and
   deriving from the detectors data describing the particle.

9. A method as claimed in claim 8 wherein the radiation scattered by individual particles is reflected by a concave reflector towards the light collectors.

10. A method as claimed in claim 9 wherein the concave reflector has an ellipsoid interior surface.

11. A method as claimed in claim 9 wherein the central axis is the reflection axis of the reflector.

12. A method as claimed in any one of claim 8 characterised in that the detectors are photomultipliers.

13. A method as claimed in claim 8 characterised in that the detectors are optical fibres connected to photomultiplers.

14. A method as claimed in claim 10 wherein the central axis is the reflection axis of the reflector.

15. A particle analyser as claimed in claim 4 wherein the central axis is the reflection axis of the reflector.

* * * * *